(12) United States Patent
Gilliam (10) Patent No.: US 10,365,229 B2
(45) Date of Patent: Jul. 30, 2019

(54) REAL-TIME CHARACTERIZATION OF PHARMACEUTICAL TABLET COATINGS USING RAMAN SPECTROSCOPY

(71) Applicant: Kaiser Optical Systems Inc., Ann Arbor, MI (US)

(72) Inventor: Sean J. Gilliam, Monroe, MI (US)

(73) Assignee: Kaiser Optical Systems, Inc., Ann Arbor, MI (US)

( * ) Notice: Subject to any disclaimer, the term of this patent is extended or adjusted under 35 U.S.C. 154(b) by 13 days.

(21) Appl. No.: 14/986,260

(22) Filed: Dec. 31, 2015

(65) Prior Publication Data

US 2017/0191947 A1    Jul. 6, 2017

(51) Int. Cl.
*G01N 21/95* (2006.01)
*G01N 21/57* (2006.01)
(Continued)

(52) U.S. Cl.
CPC ......... *G01N 21/9508* (2013.01); *G01N 21/57* (2013.01); *G01N 21/65* (2013.01);
(Continued)

(58) Field of Classification Search
CPC .... G01N 21/9508; G01N 21/57; G01N 21/65; G01N 33/15; A61J 3/005; A61K 9/28; G01J 3/44
See application file for complete search history.

(56) References Cited

U.S. PATENT DOCUMENTS 5,750,996 A * 5/1998 Drennen, III ............ G01N 1/20
250/341.2
6,453,264 B1 * 9/2002 Maguire ................. C23C 14/28
356/301
(Continued)

FOREIGN PATENT DOCUMENTS

| CN | 1309767 A | 8/2001 |
| CN | 1011460831 A | 6/2009 |
| CN | 101614667 A | 12/2009 |

OTHER PUBLICATIONS

Bawauah, Prince, "Detection of porosity of pharmaceutical compacts by terahertz radiation transmission and light reflection measurement techniques", Feb. 2014,Elsevier.*

*Primary Examiner* — Maurice C Smith
(74) *Attorney, Agent, or Firm* — John G. Posa; Belzer PC (57) ABSTRACT

Pharmaceutical tablet properties, including surface roughness, gloss and temperature, are determined in real-time using Raman spectroscopy. A plurality of coated pharmaceutical tablets are provided having a distribution of known values of a surface property to be modeled. The Raman spectrum of each coated tablet is acquired to generate a distribution of Raman spectra. A correlative model is then developed based upon the distribution of the acquired Raman spectra relative to the distribution of the known values of the measured property. The Raman spectrum of a pharmaceutical tablet is then acquired during and/or after a coating process, and the value of the surface property of the tablet is determined using the correlative model. The steps
(Continued)

associated with model development are carried out off-line, whereas the step or steps associated with acquiring the Raman spectra of the pharmaceutical tablet during (preferable) or after online coating process(es) are carried out on-line using a remote, fiber-coupled probe.

24 Claims, 6 Drawing Sheets

(51) Int. Cl.
    *G01N 21/65*     (2006.01)
    *G01N 21/88*     (2006.01)
    *G01N 33/15*     (2006.01)
    *G01N 21/84*     (2006.01)
    *A61J 3/00*     (2006.01)
    *A61K 9/28*     (2006.01)

(52) U.S. Cl.
    CPC ..... *G01N 21/8422* (2013.01); *G01N 21/8851* (2013.01); *G01N 33/15* (2013.01); *A61J 3/005* (2013.01); *A61K 9/28* (2013.01); *A61K 9/2893* (2013.01)

(56) References Cited

U.S. PATENT DOCUMENTS

| | | | | |
|---|---|---|---|---|
| 7,218,395 B2* | 5/2007 | Kaye | ............ | B07C 5/344 |
| | | | | 356/301 |
| 8,645,084 B1* | 2/2014 | Cetinkaya | ............ | G01N 29/12 |
| | | | | 702/39 |
| 2003/0147066 A1* | 8/2003 | Bruce | ............ | G01J 3/44 |
| | | | | 356/72 |
| 2006/0000470 A1* | 1/2006 | Clarke | ............ | A61J 3/00 |
| | | | | 128/200.23 |
| 2008/0034833 A1* | 2/2008 | Maier | ............ | G01J 3/02 |
| | | | | 73/1.01 |
| 2009/0123515 A1* | 5/2009 | Taylor | ............ | A61L 31/10 |
| | | | | 424/423 |
| 2012/0057018 A1* | 3/2012 | Arp | ............ | B01J 2/006 |
| | | | | 348/86 |
| 2013/0309302 A1* | 11/2013 | Funke | ............ | A61K 31/4422 |
| | | | | 424/475 |
| 2014/0183362 A1* | 7/2014 | Islam | ............ | G01J 3/453 |
| | | | | 250/338.4 |
| 2015/0335248 A1* | 11/2015 | Huang | ............ | G01N 21/65 |
| | | | | 600/476 |

* cited by examiner

*Fig. 6B*

REAL-TIME CHARACTERIZATION OF PHARMACEUTICAL TABLET COATINGS USING RAMAN SPECTROSCOPY

FIELD OF THE INVENTION

This invention relates generally to pharmaceutical tablet processing and, in particular, to real-time monitoring and determination of tablet gloss, surface roughness and tablet temperature via Raman spectroscopy.

BACKGROUND OF THE INVENTION

The coating of tablets is common in the pharmaceutical industry. Such coatings are applied for two main reasons: to achieve a desired cosmetic appearance, and, in some cases, to functionally introduce a substance such as an active pharmaceutical ingredient (API) to control drug release.

During the coating process, as the coating is added, several coating related properties change as coating is applied to the tablet in the coater. Such properties may include surface roughness, tablet gloss, and tablet temperature. The coating properties themselves, such as coating material concentration(s) and composition(s), tablet core composition, as well as the coater properties (i.e., spray rate, inlet temperature, drum speed, etc.) play a role in how these critical coating properties (values) change throughout the process, and what these values are at the end of the coating process.

For these properties, typically predefined limits are set to be reached or exceeded through the coating process. Such limits may depend upon tablet application, customs, type of product, and so forth. As such, it is critical that these properties be achieved before the tablets can be released to packaging. If one or more of the desired characteristics are not met, a batch of tablets may be rejected based upon poor coating quality, resulting in economic loss. Current practice in measuring surface roughness and tablet gloss is limited to off-line methods, typically at the end of the batch. If a small amount of sample is extracted (i.e., via a "thief") during the batch, the measurement is done tablet-by-tablet in a relatively slow offline approach. The offline assay takes time and, if properties are not developing the way they should during the coating process, in a continuous manufacturing modality, the needed process changes cannot be done in a relatively "instantaneous" manner. With offline processes, the batch may be held in quarantine, for a period of time, as measurements are acquired before the batch can be "approved" and released. The extra steps cost time and money.

In addition, knowing the temperature of the tablet during the coating process can help eliminate possible temperature induced changes to components in the tablet that might be temperature sensitive including, for example, polymorphic changes in drug-loaded coatings. Temperature measurements, if acquired, could be difficult to measure of the individual tablets themselves, and would require the use of another sensor for this measurement—resulting in additional cost.

The current practice associated with measuring tablet gloss and roughness use off-line assay methods. For example, with surface roughness, an off-line laser profilometer is used on tablets removed from the coater, either during the batch or, more commonly, after the batch of tablets are coated. Other methods to test for surface roughness, such as SEM imaging EDX analysis and Terahertz pulsed imaging (TPI), can also be utilized offline. Another possible method to quantify surface roughness is the use of near infrared spectroscopy (NIR). The NIR method is based upon a diffuse reflectance signal, and the surface roughness, when measured off-line with the coated tablet set into a fixed geometry, could possibly be extracted from the coating signal.

As for tablet gloss, this coating property is commonly measured off-line with a gloss meter—a device that delivers a beam of light at a prescribed angle onto the tablet surface at a fixed intensity. The reflected intensity is measured at the equal but opposite angle. This method also requires that the tablet to be removed from the coater for the measurement, precluding an in situ, real-time measurement.

As for tablet temperature measurements, either during coating or during tablet discharge from the coater, the common practice is to monitor temperature via a thermocouple or non-contact infrared (IR) thermometer. For the latter, the IR thermometer laser beam must be focused only onto the tablets or else the measurement will be inaccurate since the tablets/tablet bed may be at a different temperature than surrounding surfaces, especially in continuous coaters.

Both surface roughness and tablet gloss have been examined with Raman in an imaging or mapping geometry via a Raman microscope format. However, this is currently done off-line on a per-tablet basis. Tablet temperature measurements may be carried out with an IR other device projected into the tablet bed. Coating temperature may also be measured using the coater inlet and outlet air temperatures, but a complex relationship could exist between such temperatures and tablet temperature. Temperature may be measured in pseudo-real-time, if individual tablets were removed at various intervals during the process. However, this is a "destructive" modality since tablets cannot be introduced back into the process once removed for measurement.

SUMMARY OF THE INVENTION

This invention relates generally to pharmaceutical tablet inspection and, in particular, to the monitoring and determination of tablet properties using Raman spectroscopy. In preferred embodiments, such properties include surface roughness, gloss and temperature, acquired in real time using the methods and apparatus described herein.

A method aspect of the invention includes the steps of measuring a plurality of coated pharmaceutical tablets having a distribution of known values of a surface property to be modeled. The Raman spectrum of each coated tablet is acquired to generate a distribution of Raman spectra. A correlative model is developed based upon the distribution of the acquired Raman spectra relative to the distribution of the known values of the measured property. The Raman spectrum of a pharmaceutical tablet is then acquired during or after a coating process, and the value of the surface property of the tablet is determined using the correlative model.

More particularly, the method involves measuring a plurality of coated pharmaceutical tablets to determine different distributions of known values of a plurality of surface properties to be modeled, and matching the acquired Raman spectra with the known values of each surface property to be modeled. The correlative model is developed based upon the distribution in the acquired Raman spectra relative to the distribution in the known values of each measured property. In all embodiments, a univariate or multivariate model may be developed.

The steps associated with model development are preferably carried out off-line, whereas the step, or steps associated with acquiring the Raman spectra of the pharmaceutical tablet during, or after on-line coating process are carried out on-line using a remote, fiber-coupled probe. A system would further include a device for storing a dataset having a distribution of known values of a surface property acquired through the measurement of a plurality of coated pharmaceutical tablets, and a processor configured to receive the dataset and the distribution of Raman spectra to develop the correlative model. While desirable though not necessary, the same Raman spectrometer and processor may be used for off-line model development and on-line analyses.

DETAILED DESCRIPTION OF THE INVENTION

In broad an general terms, this invention makes use of Raman spectroscopy to measure surface roughness, gloss and temperature of a coated object. Though applicable to other industries, disclosed examples pertain to pharmaceutical tablet coatings.

In terms of instrumentation, a fiber-coupled Raman probe is used, preferably within the coater itself. Any suitable, commercially available Raman probe may be used, including those manufactured and sold by Kaiser Optical Systems, Inc. of Ann Arbor, Mich., further including the large-collection-area optical probe described in U.S. Pat. No. 7,148,963, the entire content of which is incorporated herein by reference.

Raman has the ability to both remotely deliver the excitation source to a particular process as well as remotely collect the Raman scattered light. With Raman's ability to detect chemical and physical information characteristic of a substance, when the probe is placed within a pharmaceutical coater (be it a batch or continuous type coater), the chemical and physical information of the tablets themselves, can be gathered in real-time, at any point in the coating process, and in a non-destructive manner.

In accordance with the invention, this real-time information feedback provides several advantages, including: (1) real-time feedback control of the coating process by monitoring the actual chemical and physical tablet information; (2) predictive determination of the end-point for individual properties; and (3) end-of-batch property determination to forgo additional off-line testing, thereby providing real-time tablet release.

With the ability to collect spectral signatures of multiple physical and chemical properties in real-time within the same spectrum, Raman has the ability to extract quantitative tablet information with regard to surface roughness, tablet gloss and tablet temperature along with % coating weight gain, as there is a direct correlation between % weight gain and tablet coating thickness.

If subsequent off-line assay reference measurements are made, correlations may be established with respect to a particular property and how that property changes relative to the acquired Raman spectrum, whether the spectrum was acquired in real-time or post-run. Such correlations may be conducted in a univariate and/or multivariate space to relate on-line Raman spectral acquisitions to a discreet quantifiable offline properties acquired offline via tablet property assay measurements. It has been shown, for example, that correlations between surface roughness, tablet gloss and/or tablet temperature can be made along with % coating weight gain to spectral changes of tablets at various quantifiable amounts of each property. Spectral preprocessing, along with multivariate analysis, such as Partial Least Squares (PLS) and/or indirect hard modeling (IHM), for example, provides information that may be plotted on a time scale to let an operator know, in real-time, the quantifiable status of surface roughness, tablet gloss and tablet temperature during and after the coating run.

In accordance with the invention, during one or more coating runs, Raman spectra are acquired at specified intervals during each run. During and/or after the coating process, several coated (or partially coated) tablet samples are quantitatively measured for surface roughness, tablet gloss and tablet temperature via off-line assays. At the specific sampling time points, the acquired Raman spectra of the samples are used to build a quantitative model that correlates each property to the Raman spectral changes occurring within the set of tablets. In a possibly less correlative modality (to online measurements), samples coated to various surface roughness, tablet gloss, etc. are analyzed with Raman offline then correlated to their offline assay values. After this model is generated, it is applied in real-time with an integrated Raman probe within a pharmaceutical coater. The specific steps of a preferred embodiment are as follows:

1a. Coat a (statistically) large set of tablets that possess various known amounts of surface roughness, tablet gloss and/or tablet temperature. Knowledge of these amounts should be determined with an off-line assay measurement device normally used to produce these values, including those devices discussed in the background of the invention.

2a. Using a pre-determined amount of total acquisition time adequate for sufficient signal-to-noise, acquire offline Raman spectra of each individual tablet for correlation to individual offline assay values.

3a. Match Raman spectral acquisitions to off-line quantitative assay values for the property to be modeled.

4a. Apply spectral preprocessing to the Raman spectral data set to minimize non-correlative changes and amplify correlative changes due to the property of importance.

5a. Determine if a univariate or multivariate modeling approach is needed. Build a correlative model to relate spectral changes to quantitative assay changes.

6a. Using modeling statistics, refine the model to enhance correlation to the assay values and/or reduce noise, bias, or other unwanted artifacts.

7a. Apply this/these model(s) to other data sets for the quantitative prediction of each assay value (whether future on-line or offline).

An alternative embodiment includes the following steps:

1b. Run a coating design of experiment (DoE) to produce a (statistically) large set of (on-line) tablets that consist of various amounts of surface roughness, tablet gloss and/or tablet temperature.

2b. During the DoE coating process, acquire Raman spectra at various time points within the coating process utilizing the same total acquisition time (especially at the start and end of the coating cycle).

3b. After the coating cycle, analyze a subset of samples from each batch via the offline assay.

4b. Match Raman spectral acquisitions and off-line quantitative values for the property to be modeled (surface roughness, tablet gloss and/or tablet temperature).

5b. Apply spectral preprocessing to the Raman spectral data set to minimize non-correlative changes and amplify correlative changes in the property of importance.

6b. Determine if a univariate or multivariate modeling approach is needed. Build a correlative model to relate spectral changes to quantitative assay changes.

7b. Using modeling statistics, refine the model to enhance correlation to the assay values and/or reduce noise, bias, or other unwanted artifacts.

8b. Apply this/these model(s) to other data sets for the quantitative prediction of each assay value (whether future on-line or offline).

The real-time information made possible by the invention allows immediate adjustments to be made, via a feedback loop, to correct properties if any move from a planned trajectory. Additionally, these properties will be known (as an aggregate) at the end of the batch, such that additional off-line measurements need not be taken. During a coating process, the Raman acquisition should be set to a proper total acquisition time to provide a certain level of precision with respect to a predicted chemical or physical measurement following preprocessing and modeling, whether univariate or multivariate. The Raman measurement has contained within it several spectral signatures from these chemical and physical properties to various signal-to-noise ratios, depending upon the strength of the signal associated with a given property and the noise within the spectrum at the relevant wavelength positions.

With all these coating properties—surface roughness, tablet gloss, and batch temperature—during and at discharge, the Raman measurement acquired during the batch contains this information. Once preprocessing is applied (mathematical manipulations of the dataset to increase variance of the particular property), these signals are then related to changes that occur in each property within the dataset. It has been determined that after pretreatments, surface roughness, tablet gloss and batch temperature can be determined in real time during the in situ measurement of the coating process.

EXAMPLES

Figure 1:
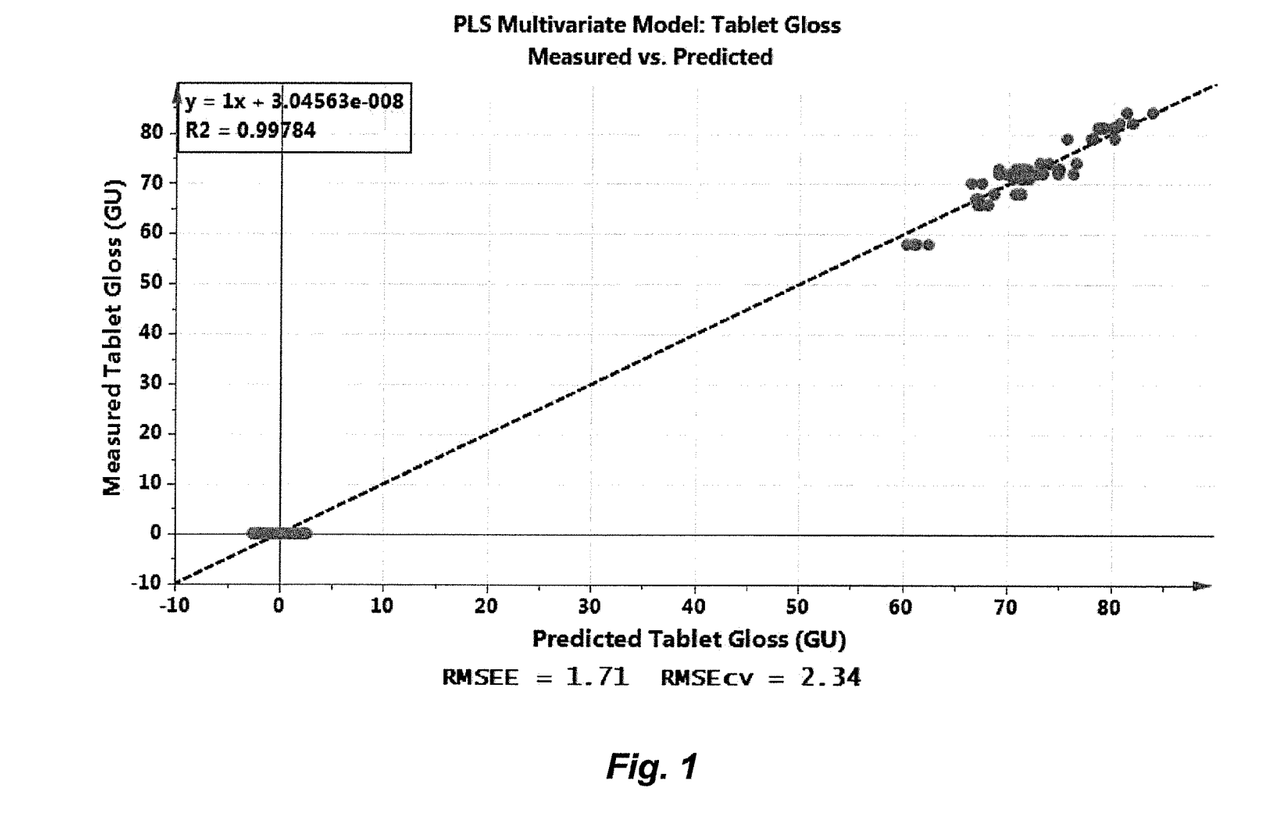
FIG. 1 is a graph that shows Raman correlation with tablet gloss during coating, plotting offline assay measured values versus online Raman predicted values.

FIG. 1 is a graph that shows Raman correlation with tablet gloss during coating, plotting offline measured values versus online predicted values. The plot displays the cross-validated predictions of online tablet gloss measurements acquired during several continuous manufacturing runs (19 trial set DoE). The dotted line indicates unity (y=x) for the correlation, whereas R2 indicates the correlation coefficient compared to unity (1.0). The model precision of the tablet gloss predictions is given both by the root mean squared error of estimation (RMSEE) and the root mean squared error of cross validation (RMSEcv).

Figure 2:
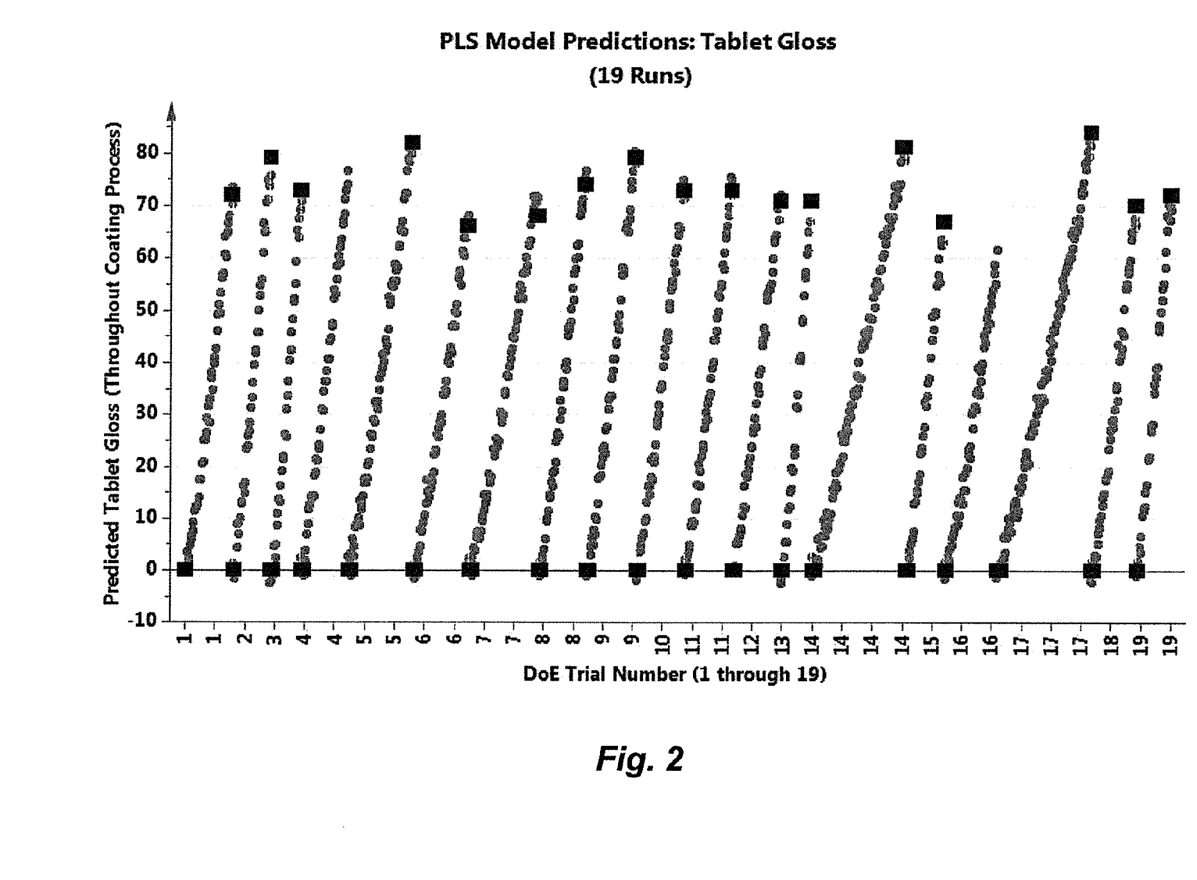
FIG. 2 is a graph that shows Raman correlation with tablet gloss during coating, plotting offline assay measured values versus online Raman predicted values for a plurality of runs.

FIG. 2 is a graph that shows Raman correlation with tablet gloss during coating, plotting offline measured values versus online predicted values throughout a 19-trail run. Both offline measured (squares) as well as online tablet gloss predictions (circles) are displayed on the plot. The online predictions were generated from the PLS gloss prediction tablet model observed earlier. As the tablet moves throughout the process, the tablet gloss should increase as the coating is applied.

Figure 3:
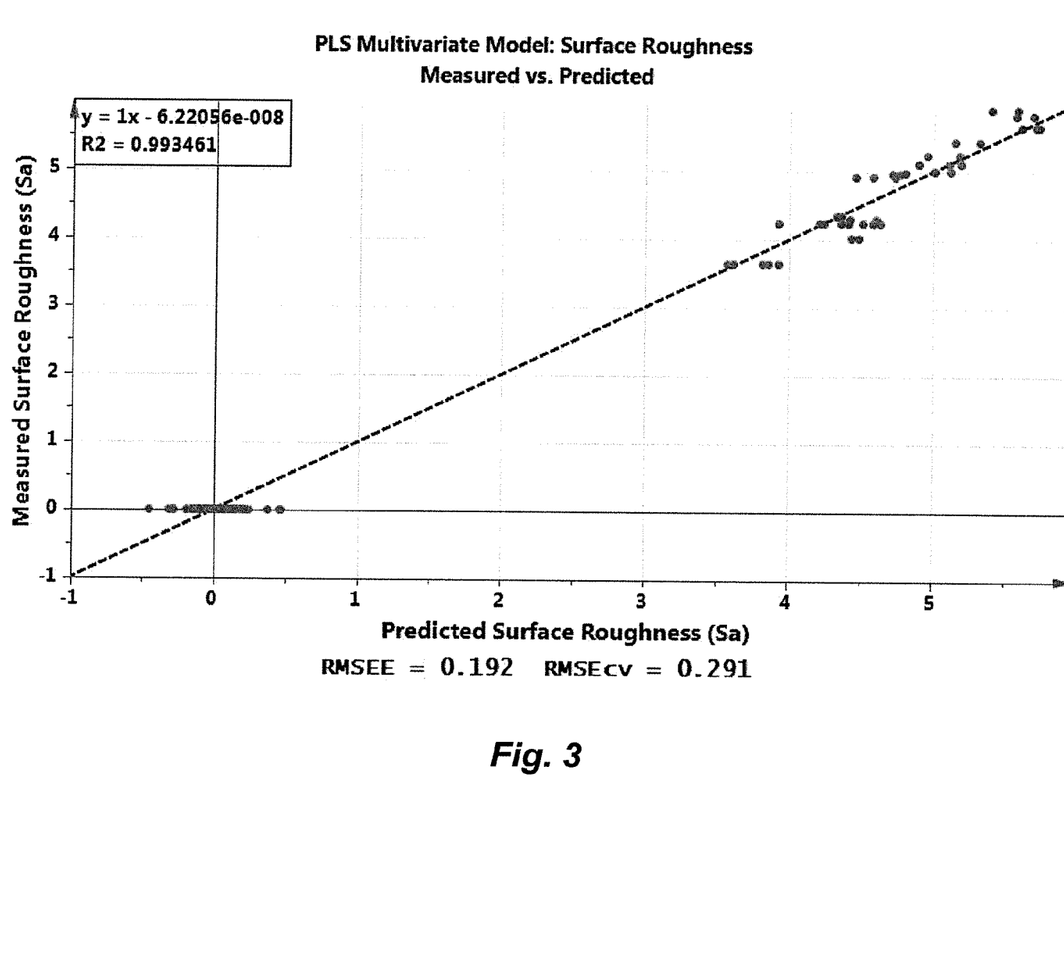
FIG. 3 is a graph that shows Raman correlation with tablet surface roughness during coating, plotting offline measured assay values versus online Raman predicted values.

FIG. 3 is a graph that shows Raman correlation with tablet surface roughness during coating, plotting offline measured values versus online predicted values. The plot displays the cross-validated predictions of online surface roughness measurements acquired during several continuous manufacturing runs (19 trial set DoE). The dotted line indicates unity (y=x) for the correlation, whereas R2 indicates the correlation coefficient compared to unity (1.0). The model precision of the surface roughness predictions is given both by the root mean squared error of estimation (RMSEE) and the root mean squared error of cross validation (RMSEcv).

Figure 4:
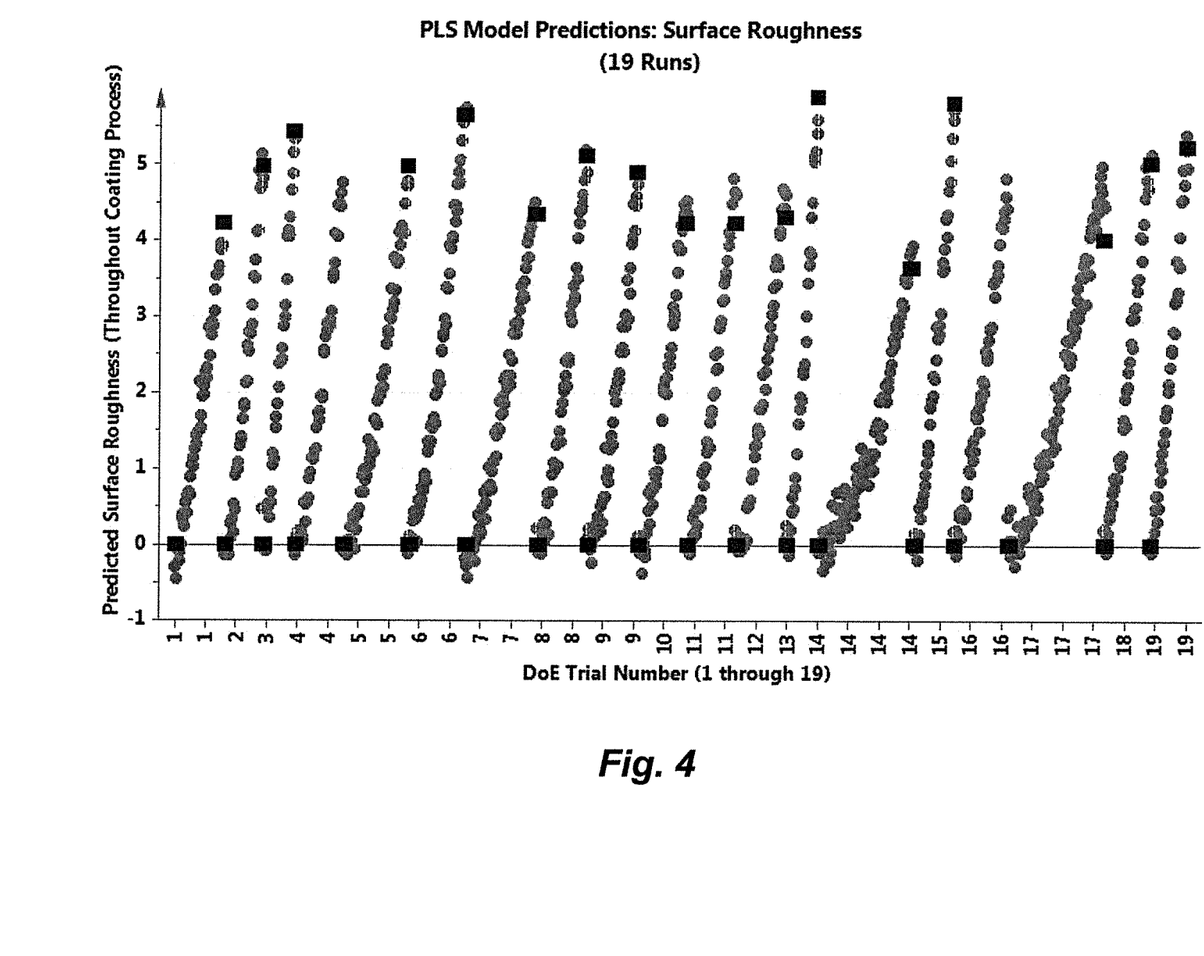
FIG. 4 is a graph that shows Raman correlation with tablet surface roughness during coating, plotting offline measured assay values versus online Raman predicted values for a plurality of runs.

FIG. 4 is a graph that shows Raman correlation with tablet surface roughness during coating, plotting offline measured values versus online predicted values throughout a 19-trail run. Both offline measured (squares) as well as online surface roughness predictions (circles) are displayed on the plot. The online predictions were generated from the PLS surface roughness tablet model observed earlier. As the tablet moves throughout the process, the surface roughness increases as the coating is applied.

Figure 5:
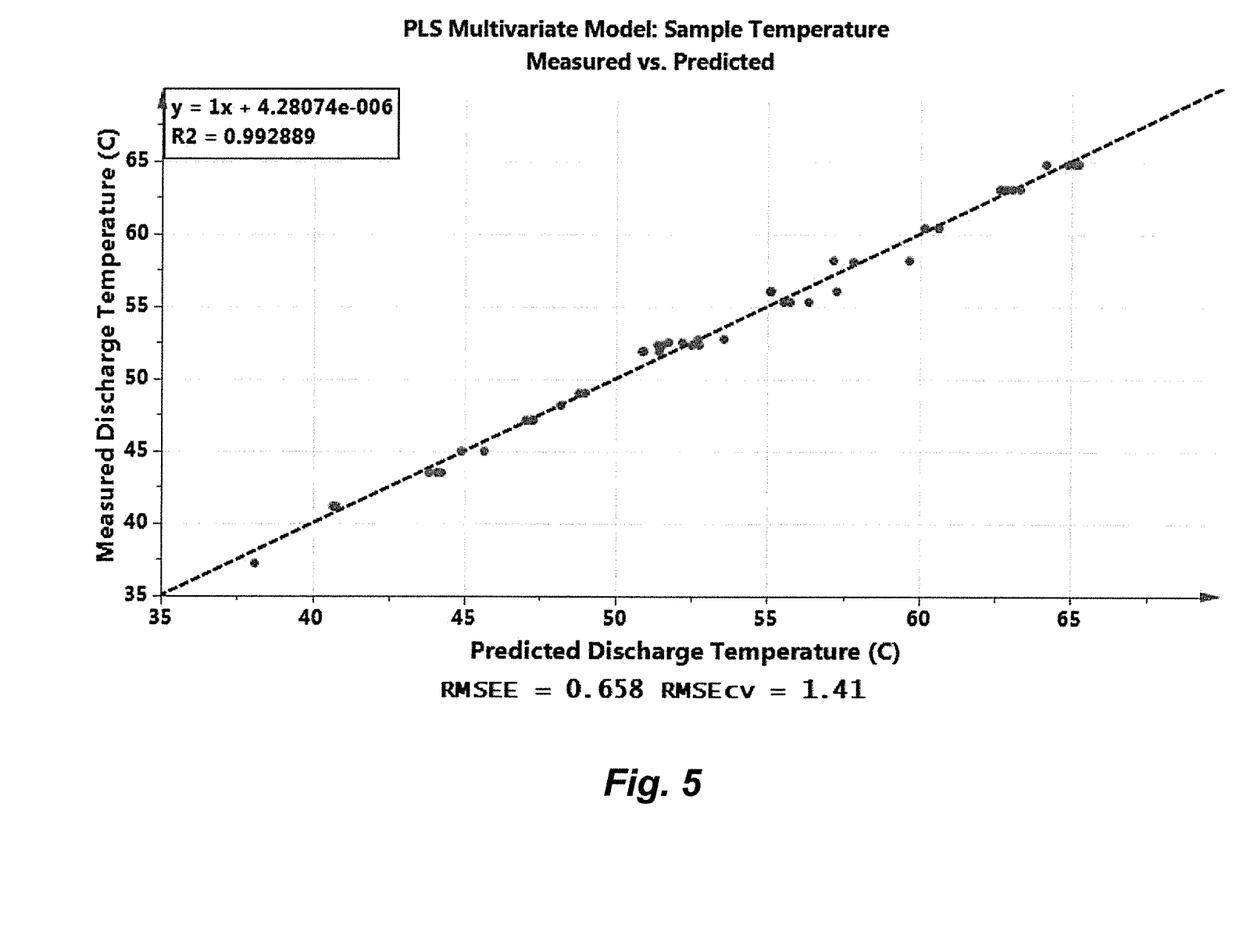
FIG. 5 is a graph that shows Raman correlation with tablet temperature during and after coating.
Figure 6A:
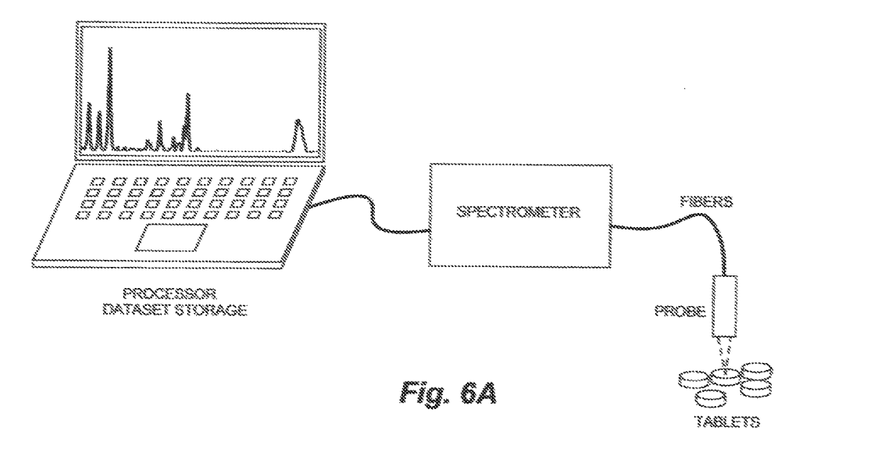
FIG. 6A is a block diagram showing hardware components associated with an offline Raman measurement probe.
Figure 6B:
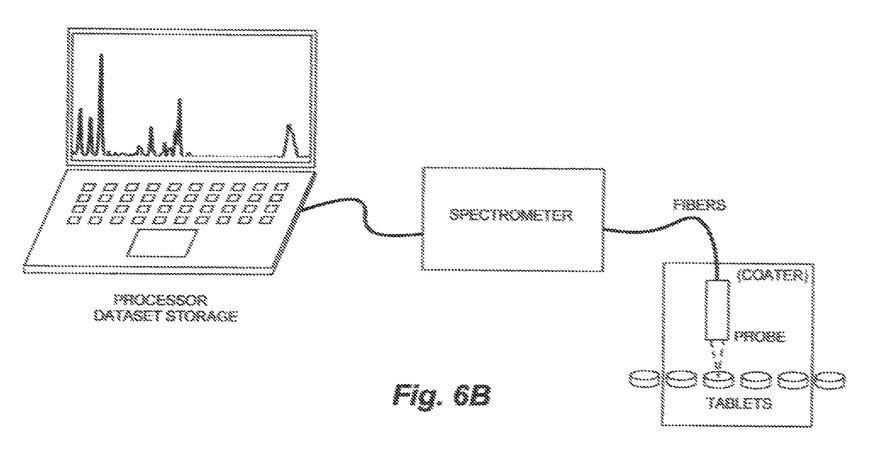
FIG. 6B is a block diagram showing hardware components associated with an online Raman measurement probe disposed within a pharmaceutical coater.

FIG. 5 is a graph that shows Raman correlation with tablet temperature during and after coating. Offline measured values are plotted against online predicted sample temperature, displaying the cross-validated predictions of online sample temperature measurements acquired during several continuous manufacturing runs (19 trial set DoE). The dotted line indicates unity (y=x) for the correlation, whereas R2 indicates the correlation coefficient compared to unity (1.0). The model precision of the sample temperature predictions is given both by the root mean squared error of estimation (RMSEE) and the root mean squared error of cross validation (RMSEcv).

In summary, the invention offers the ability to measure surface roughness, tablet gloss and/or tablet temperature alongside % tablet weight gain (i.e., coating thickness) during the coating process, with the ability to make real-time changes to the process if issues with these properties occur.

The system and method also provide the ability to know the aggregate surface roughness, tablet gloss and/or tablet temperature % tablet weight gain (i.e. coating thickness) at the end of the process to allow for real time release of the batch.

The advantages are in reducing costs involved in the offline assay (instrument purchases, instrument upkeep, operator costs involved to run the post-coating assays), while allowing a manufacturer to refine/shorten a coating process to quantitatively hit the minimum value needed for these properties, and still release the batch. This, in turn, leads to lower coating costs and improved cycle time on the coater.

The invention claimed is:

1. A method of determining a physical surface property of a coated pharmaceutical tablet, comprising the steps of:
 (a) measuring a plurality of coated pharmaceutical tablets having a distribution of known values of a surface property to be modeled, and wherein the surface property is a physical surface property separate from the chemical composition of the pharmaceutical tablet or the coating;

(b) acquiring the Raman spectrum of each coated tablet with a Raman spectrometer to generate a distribution of Raman spectra;

(c) developing a correlative model based upon the distribution of the acquired Raman spectra relative to the distribution of the known values of the measured surface property;

(d) placing a Raman probe into a pharmaceutical coater and acquiring the Raman spectrum of a pharmaceutical tablet with a Raman spectrometer coupled to the Raman probe during or after a coating process using the pharmaceutical coater;

(e) automatically determining with a processor the value of the surface property of the tablet in the pharmaceutical coater using the Raman spectrum acquired in (d) and the model developed in (c); and (f) adjusting the coating process used by the pharmaceutical coater in response to the value of the surface property determined in (e).

2. The method of claim 1, wherein the surface property is surface roughness.

3. The method of claim 1, wherein the surface property is tablet gloss.

4. The method of claim 1, wherein the surface property is temperature.

5. The method of claim 1, including the steps of:
measuring a plurality of coated pharmaceutical tablets to determine different distributions of known values of a plurality of surface properties to be modeled; and
matching the acquired Raman spectra with the known values of each surface property to be modeled; and
developing a correlative model based upon the distribution in the acquired Raman spectra relative to the distribution in the known values of each measured property.

6. The method of claim 1, including the step of using the same or a similar total Raman signal acquisition time in (b) as that used in (d).

7. The method of claim 1, including the step of using univariate or multivariate modeling in (c).

8. The method of claim 1, including the step of applying spectral preprocessing to the Raman spectra to minimize non-correlative changes or to amplify correlative changes in the property.

9. The method of claim 1, including the step of using modeling statistics to refine the model to enhance correlation or to reduce unwanted artifacts.

10. The method of claim 1, including the step of acquiring the Raman spectra of the pharmaceutical tablet during or after the coating process using a remote, fiber-coupled probe.

11. The method of claim 1, including the step of determining the amount of the surface property of the tablet in real time using the model developed in (c).

12. The method of claim 1, including the step of adjusting the coating process in response to the value of the surface property determined in (e) in real time.

13. A system for determining a physical surface property of a coated pharmaceutical tablet, comprising:

a device for storing a dataset having a distribution of known values of a surface property acquired through the measurement of a plurality of coated pharmaceutical tablets, and wherein the surface property is a physical surface property separate from the chemical composition of the pharmaceutical tablet or the coating;

a Raman spectrometer for acquiring the Raman spectrum of the coated pharmaceutical tablets to generate a distribution of Raman spectra;

a processor configured to receive the dataset and the distribution of Raman spectra and automatically develop a correlative model based upon the distribution of the acquired Raman spectra relative to the distribution of the known values of the measured property;

a Raman probe disposed in a pharmaceutical coater operative to apply a coating to a pharmaceutical tablet;

a Raman spectrometer coupled to the Raman probe for acquiring the Raman spectrum of a pharmaceutical tablet during or after a coating process using the pharmaceutical coater; and wherein the processor is operative to determine the value of the surface property of the tablet using the correlative model and the spectrum of the pharmaceutical tablet during or after the coating process.

14. The system of claim 13, wherein the surface property is surface roughness.

15. The system of claim 13, wherein the surface property is tablet gloss.

16. The system of claim 13, wherein the surface property is temperature.

17. The system of claim 13, wherein the dataset includes different distributions of known values of a plurality of surface properties to be modeled;
wherein the acquired Raman spectra are matched with the known values of each surface property to be modeled; and
the correlative model is based upon the distribution in the acquired Raman spectra relative to the distribution in the known values of each measured property.

18. The system of claim 13, wherein the total Raman signal acquisition time is substantially similar when acquiring the spectra of the measured tablets and the spectrum of the pharmaceutical tablet during or after the coating process.

19. The system of claim 13, wherein the automated modeling is univariate or multivariate.

20. The system of claim 13, wherein the processor is operative to apply spectral preprocessing to the Raman spectra to minimize non-correlative changes or to amplify correlative changes in the property.

21. The system of claim 13, wherein the processor is operative to apply modeling statistics to refine the model to enhance correlation or to reduce unwanted artifacts.

22. The system of claim 13, further including a remote, fiber-coupled probe to acquire the Raman spectra of the pharmaceutical tablet during or after the coating process.

23. The system of claim 13, wherein the acquisition of the Raman spectra of the pharmaceutical tablet during or after the coating process occurs in real time.

24. The system of claim 13, further including an informational feedback loop enabling the coating process to be adjusted in response to the value of the surface property determined during or after the coating process.

* * * * *